United States Patent [19]
McDonald

[11] 3,982,898
[45] Sept. 28, 1976

[54] APPARATUS FOR COLLECTING URINE SAMPLE

[76] Inventor: Bernard McDonald, 7700 Seville Ave., Huntington Park, Calif. 90255

[22] Filed: Jan. 8, 1976

[21] Appl. No.: 647,606

[52] U.S. Cl. ............................... 23/259; 73/421 R; 128/2 F
[51] Int. Cl.[2] .................... A61B 5/00; A61B 10/00; G01N 1/00; G01N 33/16
[58] Field of Search .......... 23/259, 253 R; 128/2 F; 73/421 R

[56] References Cited
UNITED STATES PATENTS

| | | | |
|---|---|---|---|
| 2,639,979 | 5/1953 | Goodman | 23/253 R |
| 3,774,455 | 11/1973 | Seidler et al. | 28/2 F X |
| 3,894,845 | 7/1975 | McDonald | 23/259 X |

*Primary Examiner*—Robert M. Reese
*Attorney, Agent, or Firm*—Christie, Parker & Hale

[57] ABSTRACT

A urine sample collection and testing device in which a housing has a plurality of chambers. Urine samples are collected from a common funnel unit which is mounted on top of the housing and forms a removable lid to the housing. The lid can be removed or rotated to one side relative to the housing to provide access to one or more sample compartments in the housing. A large reservoir compartment provides storage for any urine in excess of the amount used to fill the sample compartments. A forestream collection unit in the form of a collapsible bag is positioned inside the reservoir and is arranged to collect the first urine received from the funnel and to be isolated from the other compartments after receiving a predetermined amount of the initial flow through the funnel. The sample compartments permit isolation for culture growth, specific gravity measurement, sugar level measurement, and microscopic examination of sample gathered by the use of the device.

12 Claims, 8 Drawing Figures

APPARATUS FOR COLLECTING URINE SAMPLE

FIELD OF THE INVENTION

This invention relates to apparatus used in the collection and analysis of urine and, more particularly, to a compact and inexpensive disposable urine device.

BACKGROUND OF THE INVENTION

In my U.S. Pat. No. 3,894,845 there is described a urine collection and analysis device in the form of a unitary housing having a plurality of sample compartments in the housing. In my copending application Ser. No. 521,352 filed Nov. 6, 1974 now U.S. Pat. No. 3,943,770 there is described a urine collection device which incorporates a forestream collection and isolation arrangement which insures that only the midstream flow is taken as a sample.

SUMMARY OF THE INVENTION

The present invention is directed to an improved urine and collection device which combines the advantages of the above two inventions in that it provides an effective arrangement for collecting and isolating the forestream while providing separate compartments in which multiple tests can be made on the midstream sample. In addition, the present invention has the advantage that it can be easily sealed prior to use to prevent dirt or other contaminating materials from coming in contact with any of the interior surfaces of the device. In addition, it incorporates a unique funnel arrangement which simplifies the use of the device and which also serves as a lid closing off the compartments and interior of the housing.

These and other features and advantages of the present invention are achieved by providing a urine testing device comprising a housing having an open planar top. A removable funnel member extends across the top of the housing when in operative position to close off the top. The funnel member directs fluid received in the top of the funnel member through a passage extending into the top of the housing. A plurality of sample compartments in the housing receive the fluid from the passage. The initial flow of fluid through the passage is directed into a first compartment which, on becoming filled, is shut off, causing fluid to back up and fill the additional compartments, each of which is designed to carry out specific urinalysis tests.

DESCRIPTION OF THE DRAWINGS

For a more complete understanding of the invention, reference should be made to the accompanying drawings wherein.

DETAILED DESCRIPTION

Figure 1:
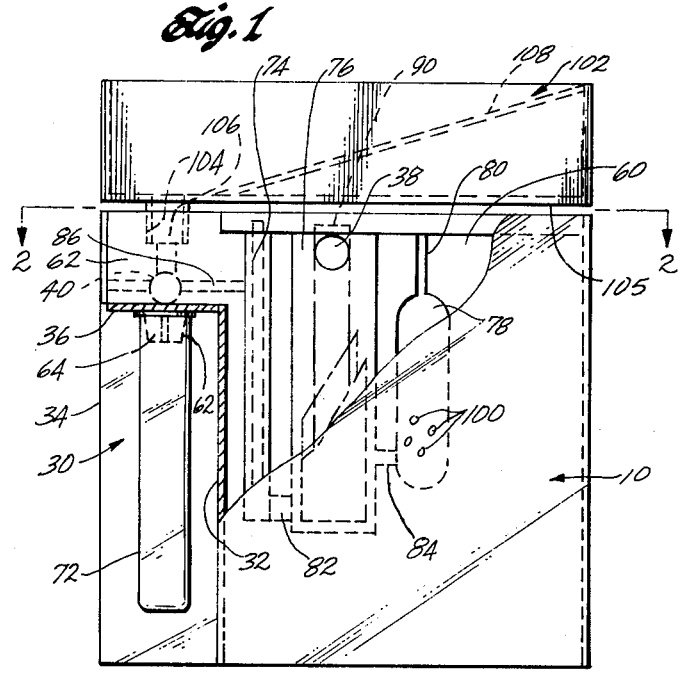
FIG. 1 is a side elevational view partly in section of one embodiment of the present invention.
Figure 2:
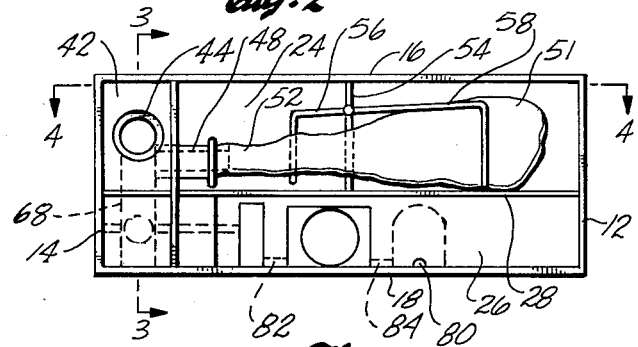
FIG. 2 is a cross-sectional view taken substantially on the line 2—2 of FIG. 1.
Figure 3:
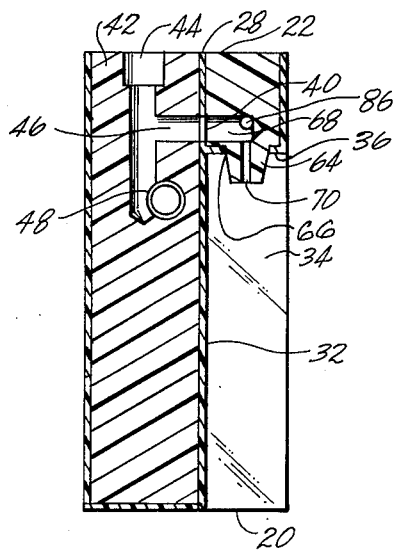
FIG. 3 is a sectional view taken substantially on the line 3—3 of FIG. 2.
Figure 4:
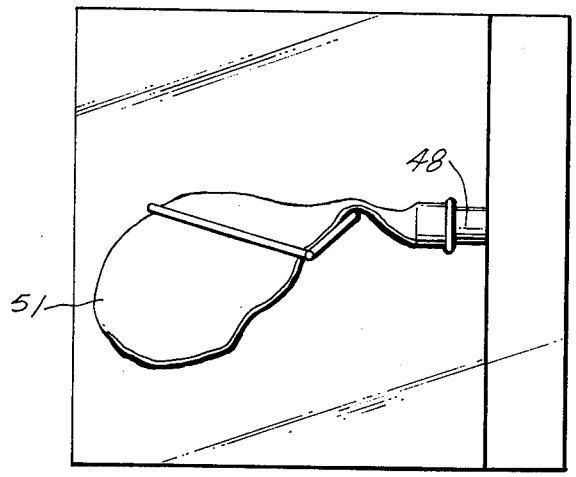
FIG. 4 is a sectional view tatken substantially on the line 4—4 of FIG. 2.

Referring to the embodiment of FIGS. 1 - 4, the numeral 10 indicates generally a housing of generally rectangular form having flat end walls 12 and 14, flat side walls 16 and 18, and a flat bottom wall 20. The tope of the housing 10, indicated at 22, is open to provide access to the interior of the housing. The walls of the housing 10 is preferably molded or otherwise formed from transparent plastic material to form a leak-proof container. The housing is divided into two compartments, 24 and 26, by an intermediate partition 28. An exterior recess 30 is formed in one corner of the housing in the side wall 18 and end wall 14, the recess 30 being formed by intersecting side walls 32 and 34 and a top wall 36. The partition 28 is provided with two openings between the compartments 24 and 26, one at 38 and the other at 40.

A rectangular block 42 is inserted in one end of the compartment 24, the block 42 having a vertical passage 44 opening through the top of the block 42 which is flush with the top 22 of the housing. The block 42 preferably is cemented in place against the inside surfaces of the comparment 24. A horizontal passage 46 extends into the block 42 and intersects the vertical passage 44. When the block 42 is in position, the passage 46 is aligned with the opening 40 in the partition 28.

A tubular nipple 48 projects from the block 42 into the compartment 24, the nipple 48 having a passage which intersects the vertical passage 44. The nipple 48 provides an outlet passage into the compartment 24. A forestream container 51, preferably in the form of a balloon or other flexible bag, has a neck portion 52 which fits over the projecting end of the nipple 48 for collecting fluid. To provide cutoff of the flow into the container 51 after a predetermined amount of fluid has entered, a cutoff mechanism is provided comprising a shaft 54 journaled at its ends in the opposing walls of the compartment 24. A first wire hook 56 extends from the shaft 54 and under the neck of the balloon. A second wire hook 58 projects from the shaft 54 and is attached to the top of the outer end of the balloon. As the balloon fills with fluid, the outer end pulls down on the hook member 58 under the added weight of the fluid, thereby raising the hook member 56 against the bottom of the neck 52 and pinching off the neck.

A molded, compartment-forming block, indicated generally at 60, is inserted in the compartment 26. A portion of the block 60 extends into the space above the wall 36 forming the top of the recess 30. The block 60 is the same width as the inner space between the side wall 18 in the partition 28. The portion 62 includes a nipple 64 which extends down into the recess 30 through a hole 66 in the wall portion 36 of the housing. A horizontal passage 68 extends through the portion 62 of the block 60 and is axially aligned with the horizontal passage 46 and opening 40 in the partition 28. A small vertical passage 70 extends up through the nipple 64 and intersects the horizontal passage 68. A sample vial or test tube 72 may be positioned in the recess 30 with the open end of the vial pressed onto the projecting nipple 64 to provide a removable sample container.

In addition, the block 60 has a plurality of vertically extending slots of different shape, such as indicated at 74, 76, and 78, which form, together with the inside of the side wall 18, a plurality of separate compartments. The upper end of the slots 74 and 76 are open while the slot 78 is provided with a restricted upper opening 80. The lower ends of the slots 74 and 76 are in fluid communication through a passage 82, while slots 76 and 78 are in fluid communication through a passage 84. A horizontal passage 86 directs fluid from the horizontal passage 68 into the slot 74.

By this arrangement, urine entering the vertical passage 44 first fills the balloon 51. After the balloon 51 is pinched off, the urine backs up into the passage 46, passing down through the passage 70 into the test vial 72. Additional flow of urine then goes through the horizontal passage 86 successively into the slots 74, 76, and 78, the level of urine rising to the opening 38 in the partition 28. Any additional flow of urine passes through the opening 38 into the compartment 24 which provides an overflow reservoir.

Figure 5:
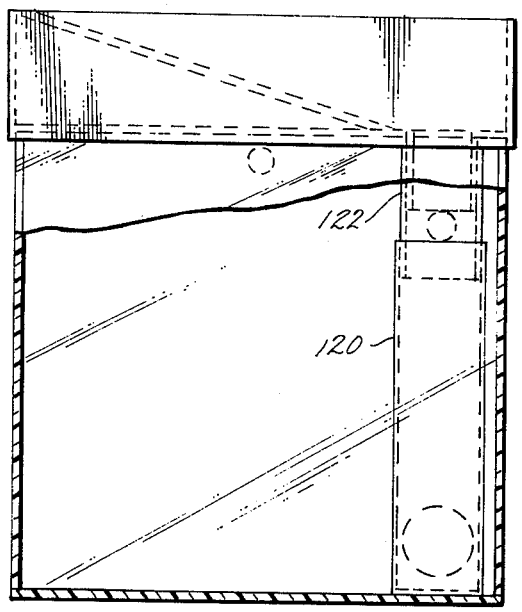
FIGS. 5 and 6 show details of a culture container in the open and closed conditions.
Figure 6:
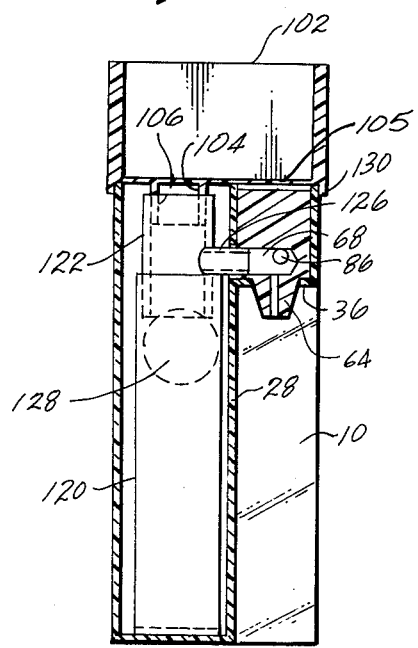

The compartment formed by the slot 74 is preferably used to receive a glass slide which can be later withdrawn and used for making microscopic examination of the urine coating on the slide. The slot 76 is preferably used for holding a removable culture vial, indicated generally at 90, which preferably is of a type shown in FIGS. 5 and 6. The culture vial includes two tubular members 92 and 94 which are each closed at one end with the other ends being telescopically joined. The open ends are truncated so that when rotated relative to each other as in the position shown in FIG. 5, and opening 96 is formed. By rotating one member through 180° relative to the other, as shown in FIG. 6, the opening 96 is closed off, forming a fully enclosed interior chamber. This chamber is filled with an agar or other culture medium and inserted in the slot 76 with the culture vial in the open condition. The culture medium then becomes exposed to the urine as it rises in the slot 76. The culture vial can then be lifted out of the slot and twisted closed to permit any microorganisms present in the urine to grow in the culture medium for subsequent analysis.

The slot 78 may be provided with a plurality of specific gravity measuring beads 100. Each color bead has a different specific gravity. By noting which color beads float and which sink in the urine sample, the specific gravity of the sample can be readily determined. In addition, a test litmus for indicating the presence of sugar may be inserted in the slot 78.

To collect the urine sample, a funnel member 102 is provided which also serves as a lid for covering the open top 22 of the housing 10. The funnel member has slide, end, and bottom walls forming a rectangular trough open at the top. The funnel member 102 has a nipple 104 projecting out of the bottom 105 which frictionally engages the upper end of the vertical passage 44 to hold the funnel member in place. A passage 106 extends through the nipple for directing fluid from the interior of the funnel member 102 into the vertical passage 44. The interior of the funnel member 102 is provided with a sloping false bottom 108 for directing the urine towards the nipple. The funnel member can be rotated out of the way around the vertical axis of the nipple to permit easy access to the test compartments formed by the slots 74 and 76. When rotated to the closed position, the funnel member closes off the open top end of the housing 10 to prevent contamination of the interior of the housing. If desired, a pressure-sensitive adhesive tape can be wrapped around the sides of the housing and funnel member to seal off the interface between the top of the housing and the bottom of the funnel member. This tape can then be removed to move the funnel member to one side and withdraw the slide and culture vial after the urine sample has been collected. Also the open top of the funnel member 102 may be sealed off by a paper diaphragm (not shown) during storage prior to use to keep dirt and other contaminants out of the funnel member. This paper seal can then be removed at the time the urine sample is collected.

Figure 7:
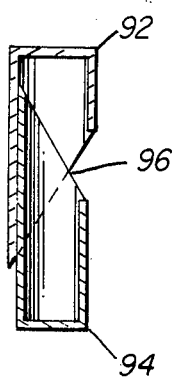
FIG. 7 is a side elevational view partly in section of an alternate embodiment of the present invention.
Figure 8:
FIG. 8 is an end view partly in section of the embodiment of FIG. 7.

An alternative embodiment is shown in FIGS. 7 and 8 which utilizes a different forestream collection arrangement. In this arrangement, the block 42 is replaced by a pair of telescopically connected tubes 120 and 122 mounted in the compartment 24. The upper end of the tube 122 receives the nipple 104 of the funnel member 102. The tube 122 has a nipple 126 extending out the side which is positioned to be inserted through the opening 40 in the partition 28 into the passage 68. A ball 128 is inserted in the tube 122 and is made of a material which has a substantially lower specific gravity than the urine. Thus the forestream of the urine sample enters directly into the tube 120 from the funnel member 102 and as the level rises, the ball 128 floats upwardly where it seats against the lower end of the tube 122, thereby sealing off the tube 122 from the tube 120. Continued flow of urine then passes through the passage 68 to fill the various compartments in the manner described above in connection with FIGS. 1 – 4. Thus the ball 128 operates to isolate the forestream of the urine sample which collects in the lower tube 120, preventing any subsequent contamination of the midstream sample entering the various test compartments.

FIGS. 7 and 8 also show a modification of the funnel member 102 in which the funnel member is formed with a projecting lip 130 around the lower periphery which extends down over the upper edge of the housing 10. The funnel member 102 is then removed by lifting it up off the top of the housing 10. The overlapping lip 130 provides a more secure connection and better seal between the funnel member 102, functioning as a lid, and the housing 10.

From the above description it will be appreciated that a highly compact urine sampling device has been provided which can be maintained in a sterile condition until used and which can be made inexpensively enough to be disposed of after use. By virtue of the relatively large funnel member, the device is easy to use during collection of the urine sample. A plurality of integral compartments are available for making separate tests without removing the urine from the device. In addition, a removable vial is provided for saving a predetermined quantity of the urine sample for additional laboratory test if desired. In addition a slide for microscopic examination and a culture are also provided.

What is claimed is:

1. Urine testing device comprising:
    a housing having an open planar top,
    a funnel member mounted on the top of the housing,
    means removably securing the funnel member to the housing, the funnel having a bottom surface overlying the open top of the housing and forming a cover for the housing, the funnel member having a passage extending into the housing for directing fluid from the funnel member into the housing, a plurality of sample compartments in the housing, and means directing fluid to said sample compartments from said passage.

2. Apparatus of claim 1 further comprising: an overflow reservoir, and means directing fluid into the overflow reservoir when said compartments have each received predetermined quantities of fluid from said passage.

3. Apparatus of claim 1 wherein at least one of said compartments comprises a vial having an open end removably attached to the housing whereby the vial can be detached when full of fluid.

4. Apparatus of claim 1 wherein at least one of said compartments is open at the top of the housing and a removable glass slide extending into the compartment through said open top.

5. Apparatus of claim 1 wherein at least one of said compartments includes means indicating the specific gravity of any urine in the compartment.

6. Apparatus of claim 1 wherein one of said compartments is open at the top of the housing, and a removable culture vial extending into compartment through said open top.

7. Apparatus of claim 1 wherein said means securing the funnel to the housing includes means for rotatably mounting the funnel member to the housing for rotaton about an axis perpendicular to said bottom surface, said passage extending along the axis of rotation.

8. Apparatus of claim further comprising: means directing the initial flow of fluid in said passage into a first compartment, and means automatically shutting off the first compartment after a predetermined quantity of fluid is received.

9. Apparatus of claim 8 wherein said first compartment includes a flexible walled bag having a neck portion, means connecting the neck portion of the bag to said passage for directing fluid from the passage into the bag, and valve means responsive to a quantity of fluid entering the bag for pinching off the neck portion of the bag to prevent further movement of fluid into or out of the bag.

10. Apparatus of claim 8 wherein said first compartment includes a tubular chamber having a reduced diameter opening at the top and a ball float in the chamber of diameter slightly larger than the reduced diameter opening for shutting off the opening when the chamber fills with urine.

11. Apparatus of claim 8 further comprising: an overflow reservoir, and means directing fluid into the overflow reservoir when said compartments have each received predetermined quantities of fluid from said passage.

12. Apparatus of claim 11 wherein said first compartment is positioned inside the reservoir.

* * * * *

UNITED STATES PATENT AND TRADEMARK OFFICE
CERTIFICATE OF CORRECTION

PATENT NO. : 3,982,898

DATED : September 28, 1976

INVENTOR(S) : Bernard McDonald

It is certified that error appears in the above-identified patent and that said Letters Patent are hereby corrected as shown below:

Column 1, line 61, "tatken" should read --taken--; Column 2, line 7, "tope" should read --top--; Column 3, line 27, "and" should read --an--; Column 3, line 30, "clossed" should read --closed--; Column 3, line 49, "slide" should read --side--; Column 5, line 24, "rotaton" should read --rotation--.

Signed and Sealed this

Eleventh Day of January 1977

[SEAL]

Attest:

RUTH C. MASON
Attesting Officer

C. MARSHALL DANN
Commissioner of Patents and Trademarks